United States Patent
Zhang et al.

(10) Patent No.: US 9,161,698 B2
(45) Date of Patent: Oct. 20, 2015

(54) MULTI-SENSOR STRATEGY FOR HEART FAILURE PATIENT MANAGEMENT

(71) Applicant: Cardiac Pacemakers, Inc., St. Paul, MN (US)

(72) Inventors: Yi Zhang, Plymouth, MN (US); Jeffrey E. Stahmann, Ramsey, MN (US); Krzysztof Z. Siejko, Maple Grove, MN (US); Ramesh Wariar, Blane, MN (US); Julie A. Thompson, Circle Pines, MN (US); John D. Hatlestad, Maplewood, MN (US); Kenneth C. Beck, Liberty, UT (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 0 days.

(21) Appl. No.: 14/248,949

(22) Filed: Apr. 9, 2014

(65) Prior Publication Data
US 2014/0221786 A1 Aug. 7, 2014

Related U.S. Application Data

(63) Continuation of application No. 12/576,453, filed on Oct. 9, 2009, now Pat. No. 8,738,119.

(60) Provisional application No. 61/104,648, filed on Oct. 10, 2008.

(51) Int. Cl.
*A61B 5/0205* (2006.01)
*A61B 5/01* (2006.01)
(Continued)

(52) U.S. Cl.
CPC ............. *A61B 5/02055* (2013.01); *A61B 5/01* (2013.01); *A61B 5/0205* (2013.01); *A61B 5/026* (2013.01);
(Continued)

(58) Field of Classification Search
CPC ............ A61B 5/0205; A61B 5/04012; A61B 5/0006; A61B 5/02405; A61B 5/0402; A61B 5/046; A61B 5/7264; A61B 5/7282; A61B 5/0245; A61B 5/021; A61B 5/0031; A61B 5/02028; A61B 2018/00839; A61B 5/02; A61B 5/0215; A61B 5/042; A61B 5/7405; A61B 5/00; A61B 5/0082; A61B 5/024; A61B 5/05; A61B 5/6846; A61B 5/72; A61N 1/3627; A61N 1/36585; A61N 1/3606; A61N 1/36139; A61N 1/365; A61N 1/36592; A61N 1/37; A61N 1/3702; A61N 1/37252; A61N 1/3937; A61N 1/3925; A61N 1/025; A61N 1/08; A61N 1/36128; A61N 1/36514; G06F 19/345; G06F 19/3418; A61M 2205/04; A61M 2205/50; A61M 2205/52; Y10T 29/49716; Y10T 428/2982
USPC ................. 600/301, 508–509, 515; 607/1–2, 607/115–116, 119
See application file for complete search history.

(56) References Cited

U.S. PATENT DOCUMENTS 4,686,987 A 8/1987 Salo et al.
5,284,136 A 2/1994 Hauck et al.
(Continued)

FOREIGN PATENT DOCUMENTS

CN 1819855 A 8/2006
WO WO-2010033928 A1 3/2010
(Continued)

OTHER PUBLICATIONS

"U.S. Appl. No. 12/563,382, Non Final Office Action mailed Feb. 24, 2012", 8 pgs.
(Continued)

*Primary Examiner* — Deborah Malamud
(74) *Attorney, Agent, or Firm* — Schwegman Lundberg & Woessner, P.A.

(57) ABSTRACT

An apparatus comprises plurality of sensors and a processor. Each sensor provides a sensor signal that includes physiological information and at least one sensor is implantable. The processor includes a physiological change event detection module that detects a physiological change event from a sensor signal and produces an indication of occurrence of one or more detected physiological change events, and a heart failure (HF) detection module. The HF detection module determines, using a first rule, whether the detected physiological change event is indicative of a change in HF status of a subject, determines whether to override the first rule HF determination using a second rules, and declares whether the change in HF status occurred according to the first and second rules.

20 Claims, 6 Drawing Sheets

(51) Int. Cl.

| | |
|---|---|
| *A61B 5/02* | (2006.01) |
| *A61B 7/04* | (2006.01) |
| *A61N 1/365* | (2006.01) |
| *A61B 5/026* | (2006.01) |
| *A61B 5/042* | (2006.01) |
| *A61B 5/145* | (2006.01) |
| *A61B 5/00* | (2006.01) |
| *A61B 5/0215* | (2006.01) |
| *A61B 5/029* | (2006.01) |
| *A61B 5/0452* | (2006.01) |
| *A61B 5/085* | (2006.01) |
| *A61B 5/12* | (2006.01) |

(52) U.S. Cl.
CPC ............ *A61B 5/02028* (2013.01); *A61B 5/042* (2013.01); *A61B 5/14542* (2013.01); *A61B 5/6869* (2013.01); *A61B 7/04* (2013.01); *A61N 1/36585* (2013.01); *A61B 5/0008* (2013.01); *A61B 5/0031* (2013.01); *A61B 5/029* (2013.01); *A61B 5/0215* (2013.01); *A61B 5/0452* (2013.01); *A61B 5/085* (2013.01); *A61B 5/121* (2013.01); *A61B 5/7275* (2013.01)

(56) References Cited

U.S. PATENT DOCUMENTS

| | | | |
|---|---|---|---|
| 5,342,406 | A | 8/1994 | Thompson |
| 5,855,593 | A | 1/1999 | Olson et al. |
| 6,076,015 | A | 6/2000 | Hartley et al. |
| 6,556,977 | B1 | 4/2003 | Lapointe et al. |
| 6,666,826 | B2 | 12/2003 | Salo et al. |
| 6,678,669 | B2 | 1/2004 | Lapointe et al. |
| 6,821,249 | B2 | 11/2004 | Casscells, III et al. |
| 7,127,290 | B2 | 10/2006 | Girouard et al. |
| 7,149,576 | B1 | 12/2006 | Baura et al. |
| 7,382,247 | B2 | 6/2008 | Welch et al. |
| 7,558,622 | B2 | 7/2009 | Tran |
| 7,992,669 | B2 | 8/2011 | Odate et al. |
| 8,319,648 | B2 | 11/2012 | Siejko et al. |
| 8,738,119 | B2 | 5/2014 | Zhang et al. |
| 2003/0008407 | A1 | 1/2003 | Fu |
| 2003/0092975 | A1 | 5/2003 | Casscells, III et al. |
| 2003/0125774 | A1 | 7/2003 | Salo |
| 2004/0127792 | A1 | 7/2004 | Siejko et al. |
| 2006/0010090 | A1 | 1/2006 | Brockway et al. |
| 2006/0161069 | A1 | 7/2006 | Li |
| 2006/0224067 | A1 | 10/2006 | Giftakis et al. |
| 2006/0265022 | A1 | 11/2006 | John et al. |
| 2006/0282000 | A1 | 12/2006 | Zhang et al. |
| 2007/0260285 | A1 | 11/2007 | Libbus et al. |
| 2007/0299356 | A1 | 12/2007 | Wariar et al. |
| 2008/0177194 | A1 | 7/2008 | Zhang et al. |
| 2008/0262533 | A1 | 10/2008 | McEwen et al. |
| 2010/0073170 | A1 | 3/2010 | Siejko et al. |
| 2010/0094102 | A1 | 4/2010 | Zhang et al. |

FOREIGN PATENT DOCUMENTS

| | | | |
|---|---|---|---|
| WO | WO-2010042790 | A2 | 4/2010 |
| WO | WO-2010042790 | A3 | 4/2010 |

OTHER PUBLICATIONS

"U.S. Appl. No. 12/563,882, Notice of Allowance mailed Jul. 19, 2012", 5 pgs.

"U.S. Appl. No. 12/563,882, Response filed May 17, 2012 to Non Final Office Action mailed Feb. 24, 2012", 16 pgs.

"U.S. Appl. No. 12/576,453 , Response filed Dec. 13, 2013 to Non Final Office Action mailed Sep. 23, 2013", 11 pgs.

"U.S. Appl. No. 12/576,453, Final Office Action mailed Nov. 23, 2012", 9 pgs.

"U.S. Appl. No. 12/576,453, Non Final Office Action mailed Sep. 23, 2013", 11 pgs.

"U.S. Appl. No. 12/576,453, Non-Final Office Action mailed Aug. 15, 2012", 8 pgs.

"U.S. Appl. No. 12/576,453, Notice of Allowance mailed Jan. 17, 2014", 7 pgs.

"U.S. Appl. No. 12/576,453, Response filed Jan. 4, 2013 to Final Office Action mailed Nov. 23, 2012", 13 pgs.

"U.S. Appl. No. 12/576,453, Response filed Jun. 27, 2012 to Restriction Requirement mailed May 31, 2012", 9 pgs.

"U.S. Appl. No. 12/576,453, Response filed Nov. 15, 2012 to Non Final Office Action mailed Aug. 15, 2012", 15 pgs.

"U.S. Appl. No. 12/576,453, Restriction Requirement mailed May 31, 2012", 7 pgs.

"Australian Application Serial No. 2009302272, Examiner Report Mailed Aug. 15, 2012", 3 pgs.

"Australian Application Serial No. 2009302272, Response filed Dec. 18, 2012 to Examiner Report mailed Aug. 15, 2012", 4 pgs.

"Chinese Application Serial No. 200980140155.2, Office Action mailed Jan. 8, 2014", With English Translation, 6 pgs.

"Chinese Application Serial No. 200980140155.2, Office Action mailed Dec. 3, 2012", With English Translation, 10 pgs.

"Chinese Application Serial No. 200980140155.2, Response filed Feb. 4, 2013 to Office Action mailed Dec. 3, 2012", (With English Translation of Claims), 11 pgs.

"European Application Serial No. 09792791.7, Office Action mailed Nov. 29, 2011", 5 pgs.

"European Application Serial No. 09792791.7, Response filed Mar. 28, 2012 to Office Action mailed Nov. 29, 2011", 6 pgs.

"International Application Serial No. PCT/US2009/057710, International Search Report mailed Dec. 4, 2009", 6 pgs.

"International Application Serial No. PCT/US2009/057710, Written Opinion mailed Dec. 4, 2009", 9 pgs.

"International Application Serial No. PCT/US2009/060118, International Preliminary Report on Patentability mailed Apr. 21, 2011", 7 pgs.

"International Application Serial No. PCT/US2009/060118, International Search Report mailed Oct. 20, 2010", 3 pgs.

"International Application Serial No. PCT/US2009/060118, Written Opinion mailed Oct. 20, 2010", 8 pgs.

Wang, C. S., et al., "Does This Dyspneic Patient in the Emergency Department Have Congestive Heart Failure?", Journal of the American Medical Association, 294(15), (2005), 1944-1956.

"Chinese Application Serial No. 200980140155.2, Office Action mailed Feb. 3, 2015", 6 pgs.

"Chinese Application Serial No. 200980140155.2, Office Action mailed Jul. 16, 2014", With English Translation, 6 pgs.

MULTI-SENSOR STRATEGY FOR HEART FAILURE PATIENT MANAGEMENT

CROSS-REFERENCE TO RELATED APPLICATIONS

This application is a continuation of U.S. application Ser. No. 12/576,453, filed on Oct. 9, 2009, now issued as U.S. Pat. No. 8,738,119, which claims the benefit of priority under 35 U.S.C. §119(e) to U.S. Provisional Application Ser. No. 61/104,648, filed Oct. 10, 2008, under 35 U.S.C. §119(e), each of which is incorporated herein by reference in its entirety.

BACKGROUND

Implantable medical devices (IMDs) include devices designed to be implanted into a patient or subject. Some examples of these devices include cardiac function management (CFM) devices such as implantable pacemakers, implantable cardioverter defibrillators (ICDs), cardiac resynchronization therapy devices (CRTs), and devices that include a combination of such capabilities. The devices can be used to treat patients using electrical or other therapies, or to aid a physician or caregiver in patient diagnosis through internal monitoring of a patient's condition. The devices may include one or more electrodes in communication with one or more sense amplifiers to monitor electrical heart activity within a patient, and often include one or more sensors to monitor one or more other patient parameters. Other examples of implantable medical devices include implantable diagnostic devices, implantable drug delivery systems, or implantable devices with neural stimulation capability.

Additionally, some IMDs detect events by monitoring electrical heart activity signals. Some IMDs derive measurements of hemodynamic parameters related to chamber filling and contractions from electrical signals provided by sensors. Sometimes patients who receive IMDs have experienced repeated heart failure (HF) decompensation or other events associated with worsening HF. Symptoms associated with worsening HF include pulmonary and/or peripheral edema, dilated cardiomyapathy, or ventricular dilation. Early attention to signs and symptoms of HF decompensation is needed for the health of the patient and allows early initiation of treatment.

OVERVIEW

This document relates generally to systems, devices, and methods for monitoring hemodynamic parameters of a patient or subject. In example 1, an apparatus comprises a plurality of sensors and a processor. Each sensor provides a sensor signal that includes physiological information and at least one sensor is implantable. The processor includes a physiological change event detection module that detects a physiological change event from a sensor signal and produces an indication of occurrence of one or more detected physiological change events, and a heart failure (HF) detection module. The HF detection module determines, using a first rule, whether the detected physiological change event is indicative of a change in HF status of a subject, determines whether to override the first rule HF determination using a second rule, and declares whether the change in HF status occurred according to the first and second rules.

In example 2, the first rule of example 1 optionally includes indicating the change in HF status when a majority of a set of detectable physiological change events is detected.

In example 3, the second rule of examples 1 and 2 optionally includes overriding a negative first rule HF determination according to the specificity of a detected physiological change event.

In example 4, the second rule of examples 1-3, optionally includes overriding a negative first rule HF determination when a condition for an S3 heart sound is met in a heart sound signal.

In example 5, the second rule of examples 1-4 optionally includes overriding a positive first rule HF determination according to a negative predictive value of a physiological change event.

In example 6, the second rule of examples 1-5 optionally includes overriding a positive first rule HF determination when a condition in a physiologic response to patient activity is met.

In example 7, the HF detection module of examples 1-6 optionally weights the second rule HF determination greater than the first rule HF determination.

In example 8, the physiological change event detection module of examples 1-7 is optionally configured to weight the detected physiological according to the sensor signal, and the HF detection module is optionally configured to determine a likelihood that the change in HF status occurred using the weight of the physiological change event, and provide an alert based on the declared HF event, wherein the alert includes an indication of the likelihood that the change in HF status occurred.

In example 9, the HF detection module of examples 1-8 is optionally configured to determine a level of urgency of the alert according to the first and second rules.

In example 10, the plurality of sensors of examples 1-9 optionally includes at least one of an implantable heart sound sensor, an implantable impedance sensor, an implantable activity sensor, an implantable respiration sensor, an implantable blood pressure sensor, an implantable electrocardiogram sensor, an implantable oxygen saturation sensor, an implantable blood flow sensor, an implantable temperature sensor; and an implantable intra-thoracic total impedance (ITTI) sensor.

In example 11, a system comprises a plurality of sensors, an implantable device, and an external device. Each of the sensors is configured to provide a sensor signal that includes physiological information. The implantable device comprises at least one of the sensors, a sampling circuit, communicatively coupled to the implantable sensors, configured to provide a sampled sensor signal, and a first communication circuit, communicatively coupled to the sampling circuit, configured to communicate the sampled sensor signal to a second device. The external device comprises a second communication circuit configured to communicate with the implantable device, and a processor, communicatively coupled to the second communication circuit. The processor includes a physiological change event detection module configured to detect a physiological change event from a sensor signal including at least one sampled sensor signal communicated from the implantable device, and produce an indication of occurrence of one or more physiological change events. The processor also includes a heart failure (HF) detection module configured to determine whether the detected physiological change events are indicative of a change in HF status using a first rule, determine whether to override the first rule HF determination using a second rule, and declare whether the change in HF status occurred according to the first and second rules.

In example 12, the first rule of example 11 optionally includes indicating a change in HF status when a majority of a set of detectable physiological change events is detected. In example 13, the second rule of examples 11 and 12 optionally includes overriding a negative first rule HF determination according to the specificity of a detected physiological change event, and overriding a positive first rule HF determination according to a negative predictive value of a physiological change event.

In example 14, a method includes sensing a plurality of physiologic sensor signals using a medical device where each sensor signal includes unique physiological information, and wherein at least one sensor is implantable, detecting which physiological change events, if any, of a set of specified physiological change events occurred using the sensor signals, determining whether the detected physiological change events are indicative of a change in HF status of a subject using a first rule, determining whether to override the first rule HF determination using a second rule, and declaring whether the change in HF status occurred according to the first and second rules.

In example 15, the determining whether the detected physiological change events are indicative of a change in HF status using a first rule of example 15 optionally includes determining that the detected physiological change events are indicative of the change in HF status when a number of detected physiological change events are a majority of a set of physiological change events that indicate the change in HF status and are detectable by the medical device.

In example 16, the determining whether to override the first rule HF determination using a second rule of examples 14 and 15 optionally includes overriding a negative first rule HF determination according to a specificity of a detected physiological change event.

In example 17, the determining whether to override the first rule HF determination using a second rule of examples 14-16 optionally includes overriding the negative first rule HF determination when a condition for an S3 heart sound is met in a heart sound signal.

In example 18, the determining whether to override the first rule HF determination using a second rule of examples 14-17 optionally includes overriding a positive first rule HF determination according to a negative predictive value of a detected physiological change event.

In example 19, the determining whether to override the first rule HF determination using a second rule of examples 14-18 optionally includes overriding a positive first rule HF determination when a condition in a physiologic response to patient activity is met.

In example 20, the determining whether to override the first rule HF determination using a second rule of examples 14-19 optionally includes weighting the second rule HF determination greater than the first rule HF determination.

In example 21, the determining which physiological change events occurred of examples 14-20 optionally includes weighting the detected physiological change event according to the sensor signal, and wherein the method includes providing an alert based on the declared change in HF status, wherein the alert includes an indication of a likelihood that the change in HF status occurred.

In example 22, the method of example 21 optionally includes determining a level of urgency of the alert according to the first and second rules.

In example 23, the sensing a plurality of physiological sensor signals of examples 14-22 optionally includes sensing at least one of an implantable heart sound sensor, an implantable impedance sensor, an implantable activity sensor, an implantable respiration sensor, an implantable blood pressure sensor, an implantable electrocardiogram sensor, an implantable oxygen saturation sensor, an implantable blood flow sensor, an implantable temperature sensor, and an implantable intra-thoracic total impedance (ITTI) sensor.

In example 24, the method of examples 14-23 optionally includes sampling at least one physiological sensor signal using an implantable device, communicating the sampled physiological sensor signal from the implantable device to an external device, and optionally includes using the external device to detect a physiological change event from the sampled signal, determine whether a detected event is indicative of a change in HF status, and declare whether the change in HF status occurred according to the first and second rules.

This section is intended to provide an overview of subject matter of the present patent application. It is not intended to provide an exclusive or exhaustive explanation of the invention. The detailed description is included to provide further information about the present patent application.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

DETAILED DESCRIPTION

An implantable medical device (IMD) may include one or more of the features, structures, methods, or combinations thereof described herein. For example, a cardiac monitor or a cardiac stimulator may be implemented to include one or more of the advantageous features or processes described below. It is intended that such a monitor, stimulator, or other implantable or partially implantable device need not include all of the features described herein, but may be implemented to include selected features that provide for unique structures or functionality. Such a device may be implemented to provide a variety of therapeutic or diagnostic functions. It would be desirable for an IMD to provide monitoring of HF in patients who have experienced HF or are at risk of developing HF.

Figure 1:
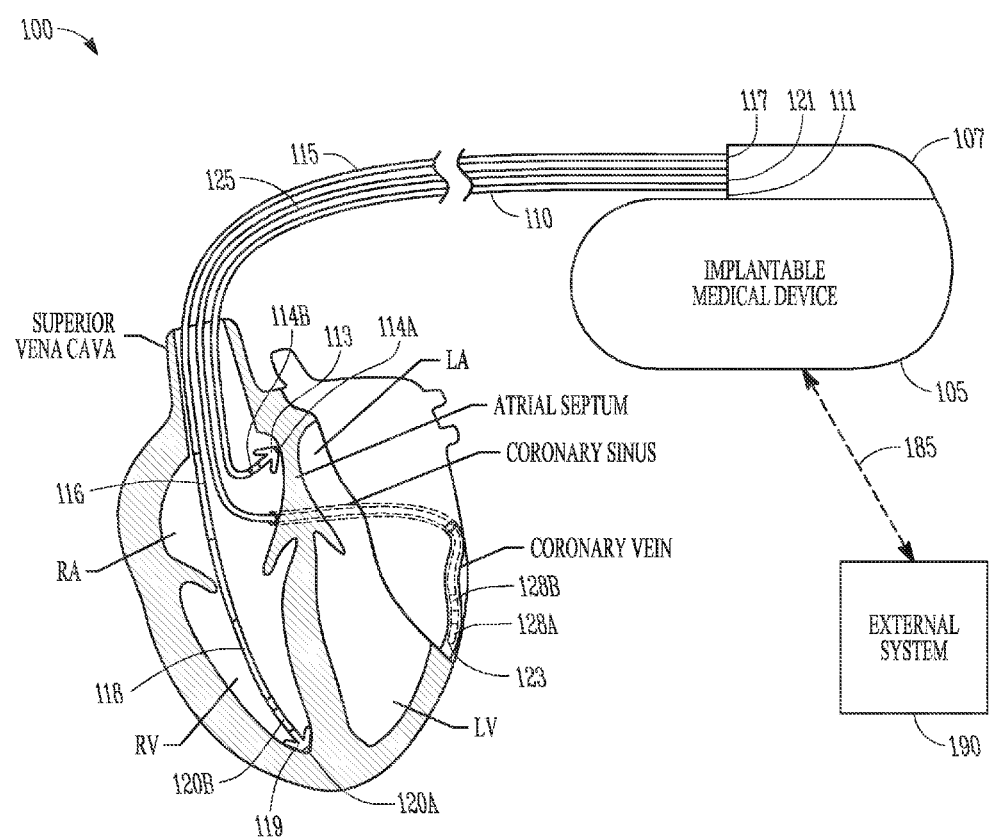
FIG. 1 is an illustration of portions of a system that uses an IMD.

FIG. 1 is an illustration of portions of a system 100 that uses an IMD 105. Examples of IMD 105 include, without limitation, a pacemaker, a cardioverter, a defibrillator, a cardiac resynchronization therapy (CRT) device, and other cardiac monitoring and therapy delivery devices, including cardiac devices that include or work in coordination with one or more neuro-stimulating devices, drugs, drug delivery systems, or other therapies. As one example, the system 100 shown is used to treat a cardiac arrhythmia. The IMD 105 typically includes an electronics unit coupled by one or more cardiac leads 110, 115, 125, to a heart of a patient or subject. The electronics unit of the IMD 105 typically includes components that are enclosed in a hermetically-sealed canister or "can." The system 100 also typically includes an IMD programmer or other external system 190 that communicates one or more wireless signals 185 with the IMD 105, such as by using radio frequency (RF) or by one or more other telemetry methods.

The example shown includes right atrial (RA) lead 110 having a proximal end 111 and a distal end 113. The proximal end 111 is coupled to a header connector 107 of the IMD 105. The distal end 113 is configured for placement in the RA in or near the atrial septum. The RA lead 110 may include a pair of bipolar electrodes, such as an RA tip electrode 114A and an RA ring electrode 114B. The RA electrodes 114A and 114B are incorporated into the lead body at distal end 113 for placement in or near the RA, and are each electrically coupled to IMD 105 through a conductor extending within the lead body. The RA lead is shown placed in the atrial septum, but the RA lead may be placed in or near the atrial appendage, the atrial free wall, or elsewhere.

The example shown also includes a right ventricular (RV) lead 115 having a proximal end 117 and a distal end 119. The proximal end 117 is coupled to a header connector 107. The distal end 119 is configured for placement in the RV. The RV lead 115 may include one or more of a proximal defibrillation electrode 116, a distal defibrillation electrode 118, an RV tip electrode 120A, and an RV ring electrode 120B. The defibrillation electrode 116 is generally incorporated into the lead body such as in a location suitable for supraventricular placement in the RA and/or the superior vena cava. The defibrillation electrode 118 is incorporated into the lead body near the distal end 119 such as for placement in the RV. The RV electrodes 120A and 120B may form a bipolar electrode pair and are generally incorporated into the lead body at distal end 119. The electrodes 116, 118, 120A, and 120B are each electrically coupled to IMD 105, such as through one or more conductors extending within the lead body. The proximal defibrillation electrode 116, distal defibrillation electrode 118, or an electrode formed on the can of IMD 105 allow for delivery of cardioversion or defibrillation pulses to the heart.

The RV tip electrode 120A, RV ring electrode 120B, or an electrode formed on the can of IMD 105 allow for sensing an RV electrogram signal representative of RV depolarizations and delivering RV pacing pulses. In some examples, the IMD includes a sense amplifier circuit to provide amplification and/or filtering of the sensed signal. RA tip electrode 114A, RA ring electrode 114B, or an electrode formed on the can of IMD 105 allow for sensing an RA electrogram signal representative of RA depolarizations and allow for delivering RA pacing pulses. Sensing and pacing allows the IMD 105 to adjust timing of the heart chamber contractions. In some examples, the IMD 105 can adjust the timing of ventricular depolarizations with respect to the timing of atrial depolarizations by sensing electrical signals in the RA and pacing the RV at the desired atrial-ventricular (AV) delay time.

A left ventricular (LV) lead 125 can include a coronary pacing or sensing lead that includes an elongate lead body having a proximal end 121 and a distal end 123. The proximal end 121 is coupled to a header connector 107. A distal end 123 is configured for placement or insertion in the coronary vein. The LV lead 125 may include an LV tip electrode 128A and an LV ring electrode 128B. The distal portion of the LV lead 125 is configured for placement in the coronary sinus and coronary vein such that the LV electrodes 128A and 128B are placed in the coronary vein. The LV electrodes 128A and 128B may form a bipolar electrode pair and are typically incorporated into the lead body at distal end 123. Each can be electrically coupled to IMD 105 such as through one or more conductors extending within the lead body. LV tip electrode 128A, LV ring electrode 128B, or an electrode formed on the can of the IMD 105 allow for sensing an LV electrogram signal representative of LV depolarizations and delivering LV pacing pulses.

The IMDs may be configured with a variety of electrode arrangements, including transvenous, epicardial electrodes (i.e., intrathoracic electrodes), and/or subcutaneous, non-intrathoracic electrodes, including can, header, and indifferent electrodes, and subcutaneous array or lead electrodes (i.e., non-intrathoracic electrodes). Some IMDs are able to sense signals representative of cardiac depolarizations using electrodes without leads.

As discussed previously, early attention to signs and symptoms of HF decompensation is needed for optimal health of the patient. One of the challenges in detection of a change in status of HF (e.g., worsening) is to reduce false alarms while ensuring that actual or true changes in status are detected accurately. The systems and methods described below monitor the patient and generate alerts to the clinician when an impending HF event is detected. Because the alerts require a clinician's timely review of patient-related information to determine what triggered the alert and to identify the appropriate response, false alarms cause the unnecessary expenditure of healthcare resources. Additionally, too many false alarms may cause the clinician to ignore all alerts as "nuisance alarms" including detections which are true, thereby defeating the benefit of the system.

Figure 2:
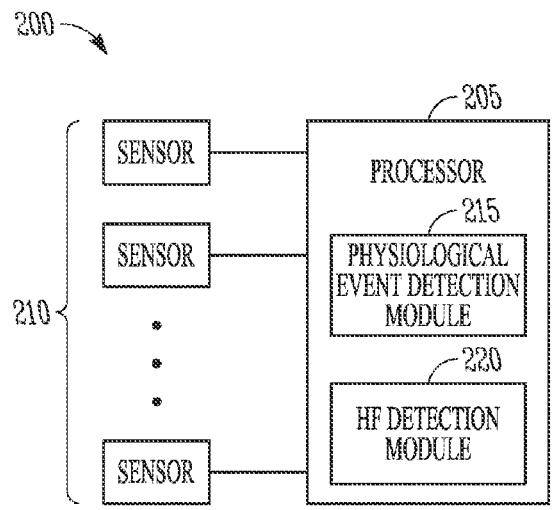
FIG. 2 is a block diagram of an example of a device to monitor HF of a subject.

FIG. 2 is a block diagram of an example of a device 200 to monitor HF of a patient or subject. The device 200 includes a processor 205 and a plurality of sensors 210 communicatively coupled to the processor 205. At least one of the sensors 210 is an implantable sensor. The processor 205 may include a microprocessor, a digital signal processor, application specific integrated circuit (ASIC), microprocessor, or other type of processor, interpreting or executing instructions in software or firmware. Each of the sensors 210 provides a sensor signal that includes physiological information. The communicative coupling allows the processor 205 and the sensors 210 to communicate even though there may be intervening circuitry between the processor 205 and the sensors 210.

In some examples, the sensors 210 include an implantable heart sound sensor. Heart sounds are associated with mechanical vibrations from activity of a patient's heart and the flow of blood through the heart. Heart sounds recur with each cardiac cycle and are separated and classified according to the activity associated with the vibration. The first heart sound (S1) is the vibrational sound made by the heart during tensing of the mitral valve. The second heart sound (S2) marks the closing of the aortic valve and the beginning of diastole. The third heart sound (S3) and fourth heart sound (S4) are related to filling pressures of the left ventricle during diastole. A heart sound sensor produces an electrical signal which is representative of mechanical activity of a patient's heart. The heart sound sensor is disposed in a heart, near the heart, or in another location where the acoustic energy can be sensed. In some examples, the heart sound sensor includes an accelerometer disposed in or near a heart. In another example, the heart sound sensor includes an accelerometer disposed in the IMD. In another example, the heart sound sensor includes a microphone disposed in or near a heart.

Many types of physiological information can be included in a signal provided by a heart sound sensor. For example, the presence of an S3 heart sound may be an indication of elevated filling pressure. Thus, the development of, or a change in, an S3 heart sound may indicate a change in status of HF of the subject. An approach for monitoring heart sounds is found in Siejko et al., U.S. Patent Application Publ. No. 2004/0127792, entitled "Method and Apparatus for Monitoring of Diastolic Hemodynamics," filed Dec. 30, 2002, which is incorporated herein by reference in its entirety.

In some examples, the sensors 210 include a respiration sensor. An example of an implantable respiration sensor is an intra-thoracic total impedance sensor ITTI. The signal provided by the ITTI sensor provides physiological information that can be used to measure respiration parameters such as respiratory rate, tidal volume, minute respiration volume, and derived parameters such as the ratio of respiratory rate over tidal volume. An approach to measuring thoracic impedance is described in Hartley et al., U.S. Pat. No. 6,076,015, "Rate Adaptive Cardiac Rhythm Management Device Using Transthoracic Impedance," filed Feb. 27, 1998, which is incorporated herein by reference in its entirety. Measuring respiration parameters can be useful in detecting abnormal breathing.

The sensor signal provided by an ITTI sensor can also provide information related to a change in fluid build-up in the thorax region of the subject. A decrease in impedance may indicate an increase in interstitial fluid build-up due to pulmonary edema.

In some examples, the sensors 210 include an implantable patient activity sensor. An example of an implantable patient activity sensor is an accelerometer. The combination of a respiration sensor and an activity sensor, and/or the combination of a heart rate sensor and an activity sensor, is useful for monitoring a patient's physiological response to activity (PRA), such as to detect one or both of abnormal breathing and abnormal reflex sympathetic activation due to activity. The device 200 may include other types of sensors, such as those discussed later in this document.

The processor 205 includes a physiological change event detection module 215. Modules can be software, hardware, firmware or any combination thereof. Multiple functions can be performed in one or more modules as desired. The physiological change event detection module 215 detects a physiological change event from a sensor signal. A physiological change event refers to a detected change in subject physiology. In certain examples, the physiological change event detection module 215 detects elevated filling pressure from a heart sound sensor signal. In certain examples, the physiological change event detection module 215 detects thoracic fluid from an ITTI sensor signal. In certain examples, the physiological change event detection module 215 detects a change in heart rate using an electrocardiogram sensor. In certain examples, the physiological change event detection module 215 detects abnormal breathing such as tachypnea, rapid shallow breathing, apnea, hypopnea, or hyperventilation from a respiration sensor signal. In certain examples, the physiological change event detection module 215 detects one or both of abnormal breathing and abnormal reflex sympathetic activation during patient activity using a respiration sensor signal, an electrocardiographic signal, and a patient activity sensor signal. The physiological change event detection module 215 also produces an indication of occurrence of one or more detected physiological change events.

The processor 205 includes a heart failure (HF) detection module 220. The HF detection module 220 determines whether the detected physiological change event is indicative of a change in HF status of the patient. To make the determination, the HF detection module 220 includes a sensor fusion algorithm used to blend the indications from the physiological change event detection module 215. The algorithm includes application of two rules. The HF detection module 220 declares whether the change in HF status occurred according to the first and second rules.

The first rule is applied to the detected physiological change events to determine whether they are indicative of a change in HF status of a subject. In some examples, the HF detection module 220 makes an individual assessment of HF from the information received from each sensor. In some examples, the first rule includes a majority rule and indicates a change in patient HF status when detecting a majority of a set of detectable physiological change events that indicate HF (e.g., more events are detected that are indicative HF than are events that either are not indicative of HF or are contraindicative of HF).

The second rule determines whether to override the first rule HF determination. In some examples, the second rule includes overriding a negative first rule HF determination according to the specificity of a detected physiological change event. For example, application of the first rule may indicate no change in HF status of the patient. However, one of the sensors may provide such a strong indication of HF that the first rule HF determination should be overridden. An example of a strong indication of a change in HF status is development of an S3 heart sound that previously was not present. The second rule may override the negative first rule HF determination when a condition for an S3 heart sound is met in the heart sound sensor signal. In certain examples, the HF detection module 220 weights the second rule HF determination greater than the first rule HF determination to cause the override or to inhibit the override. This provides a method of gradation of the possible overriding events.

In some examples, the second rule includes overriding a positive first rule HF determination according to a negative predictive value of a physiological change event. For example, application of the first rule may indicate a change in HF status of the patient, but one of the sensors may provide a strong indication that no change in status occurred and the first rule HF determination should be overridden. An example of a strong indication of no change in HF status is when a condition in a physiologic response to patient activity is met, such as when a heart rate sensor (e.g., an implantable electrocardiogram sensor) indicates that a patient's heart rate has an appropriate response to an increase in patient activity indicated by an activity sensor. In such a case, the second rule may include overriding the positive first rule HF determination. In some examples, the HF detection module 220 provides an alert based on the declared HF event.

Figure 3:
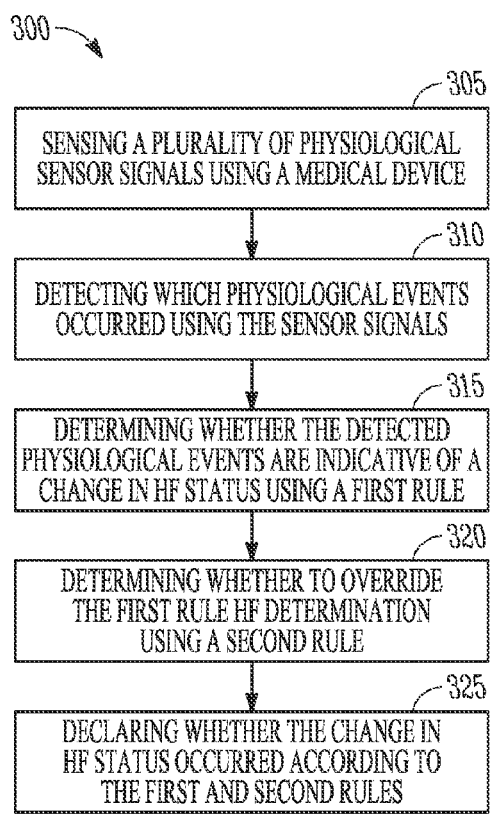
FIG. 3 shows a flow diagram of a method to monitor HF of a subject.

FIG. 3 shows a flow diagram of a method 300 to monitor HF of a subject. At block 305, a plurality of physiologic sensor signals are sensed using a medical device and at least one sensor is implantable. Each sensor signal is detected from a different sensor and includes physiological information. At block 310, the sensor signals are used to determine which physiological change events occurred (if any) of a set of specified physiological change events. At block 315, whether the detected physiological change events are indicative of a change in HF status of the subject is determined using a first rule. At block 320, whether to override the first rule HF determination is determined using a second rule. At block 325, whether a change in HF status occurred is declared according to the first and second rules.

Table 1 shows an example of sensor fusion to determine a change in HF status. Four sensors are included the example: a heart sound sensor to detect the S3 heart sound, an ITTI sensor, a respiration sensor, and physiological response to activity (PRA) sensor. Binary logic is used to determine the indication from an individual sensor. For example, a sensor is deemed to indicate HF ("Y") if the sensor output satisfies a threshold condition for indicating HF, and is deemed to not indicate HF ("N") otherwise.

TABLE 1

|    | S3 | ITTI | Resp | PRA | Alert | Exceptions |
|----|----|------|------|-----|-------|------------|
| 1  | Y  | Y    | Y    | Y   | Y     |            |
| 2  | Y  | Y    | Y    | N   | Y     | S3 high spec overrides PRA |
| 3  | Y  | Y    | N    | Y   | Y     |            |
| 4  | Y  | Y    | N    | N   | Y     |            |
| 5  | Y  | N    | Y    | Y   | Y     |            |
| 6  | Y  | N    | Y    | N   | Y     | S3 high spec overrides PRA |
| 7  | Y  | N    | N    | Y   | Y     |            |
| 8  | Y  | N    | N    | N   | N     |            |
| 9  | N  | Y    | Y    | Y   | Y     |            |
| 10 | N  | Y    | Y    | N   | N     | PRA high NPV overrides |
| 11 | N  | Y    | N    | Y   | Y     |            |
| 12 | N  | Y    | N    | N   | N     |            |
| 13 | N  | N    | Y    | Y   | Y     |            |
| 14 | N  | N    | Y    | N   | N     |            |
| 15 | N  | N    | N    | Y   | N     |            |
| 16 | N  | N    | N    | N   | N     |            |

As an illustrative example, the heart sensor (e.g., an accelerometer) is deemed to indicate worsening HF when the heart sound sensor signal indicates an S3 heart sound having an amplitude greater than a threshold (e.g., 5 mg (acceleration in g's) or 15 mg), and a change in the amplitude of 100% (e.g., doubling). The ITTI sensor is deemed to indicate worsening HF when the impedance sensor signal changes by greater than 10%. The respiration sensor is deemed to indicate worsening HF when the respiration sensor signal indicates a change in the determined respiration rate of greater than 5 breaths per minute, or when the determined respiration rate exceeds 30 breaths per minute. The PRA sensor is deemed to indicate worsening HF when the sensor signal or signals indicate the patient's response to physical activity has increased by more than 20%, or when a normalized ratio of breathing volume (e.g., minute volume) to activity exceeds a threshold ratio value.

A majority rule is used to determine whether a change in HF status occurred and an alert should be generated. Normally, when the outputs of at least two sensors satisfy the threshold condition, the alert is generated. This would be an example of an alert generated by the first rule. However, as indicated in the table, there are exceptions that may override the majority rule. Line 10 of the table would normally generate an alert due to the ITTI sensor and the respiration sensor indication a change in HF. However, a negative indication from the PRA sensor has such strong negative predictor value (NPV) that the negative PRA indication overrides the majority rule. This is an example of a second HF rule (PRA's NPV) overriding a first HF rule (the majority rule).

A change in the S3 heart sound that satisfies the threshold criterion indicates worsening HF with high specificity. The S3 heart sound has such strong positive predictor value (PPV) that the positive S3 indication overrides a negative PRA indication (as shown in lines 2 and 6 of Table 1).

Figure 4:
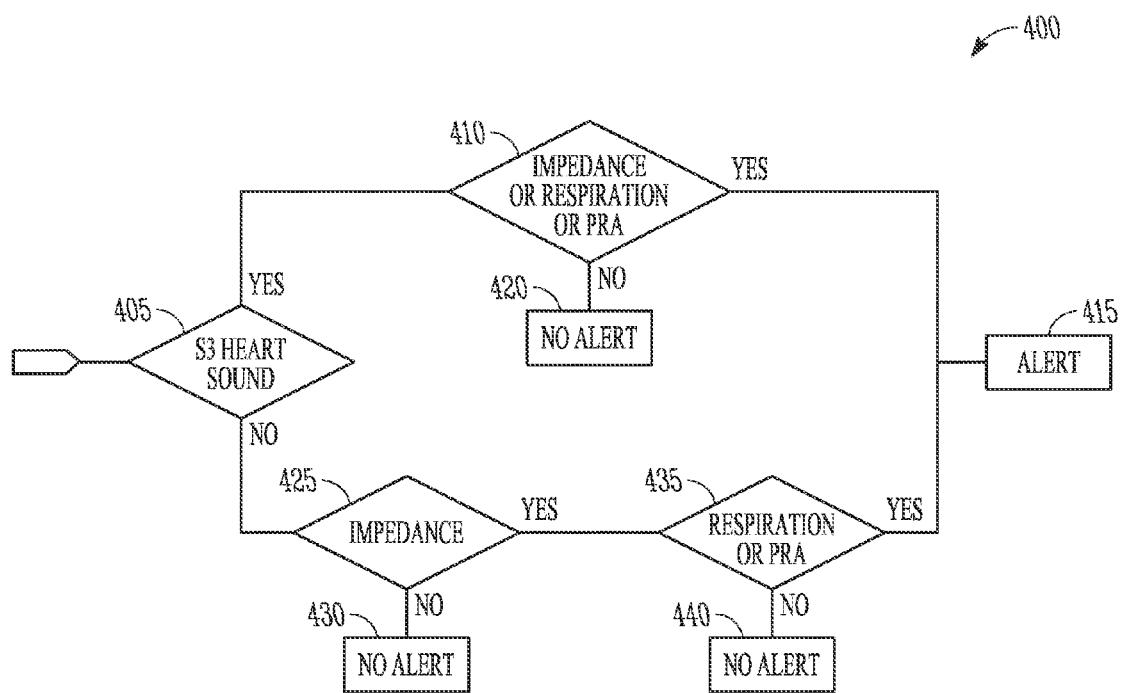
FIG. 4 is a flow diagram of an example of a method to determine whether a change occurred in the status of HF of a subject.

FIG. 4 is a flow diagram of an example of a method 400 to determine whether a change occurred in the status of HF of a subject. In the method 400, binary decision making is applied to the sensor outputs. At block 405, it is determined whether the heart sound sensor signal provides a positive indication of HF, such as an increase in S3 heart sound amplitude. If it does, at block 410 it is determined if another sensor provides a positive indication of HF. If yes, an alert is generated at block 415; if not, no alert is indicated at block 420.

If no S3 heart sound is included in the sensor signal, it is determined at block 425 whether the impedance sensor (e.g., ITTI) provides a positive indication of HF. If not, no alert is indicated at block 430. If the impedance sensor does provide a positive indication of HF, at block 435 it is determined whether one of the respiration or the PRA sensor provides a positive indication of HF. If not, no alert is indicated as shown in block 440. If so, then an alert is generated at block 415.

Figure 5:
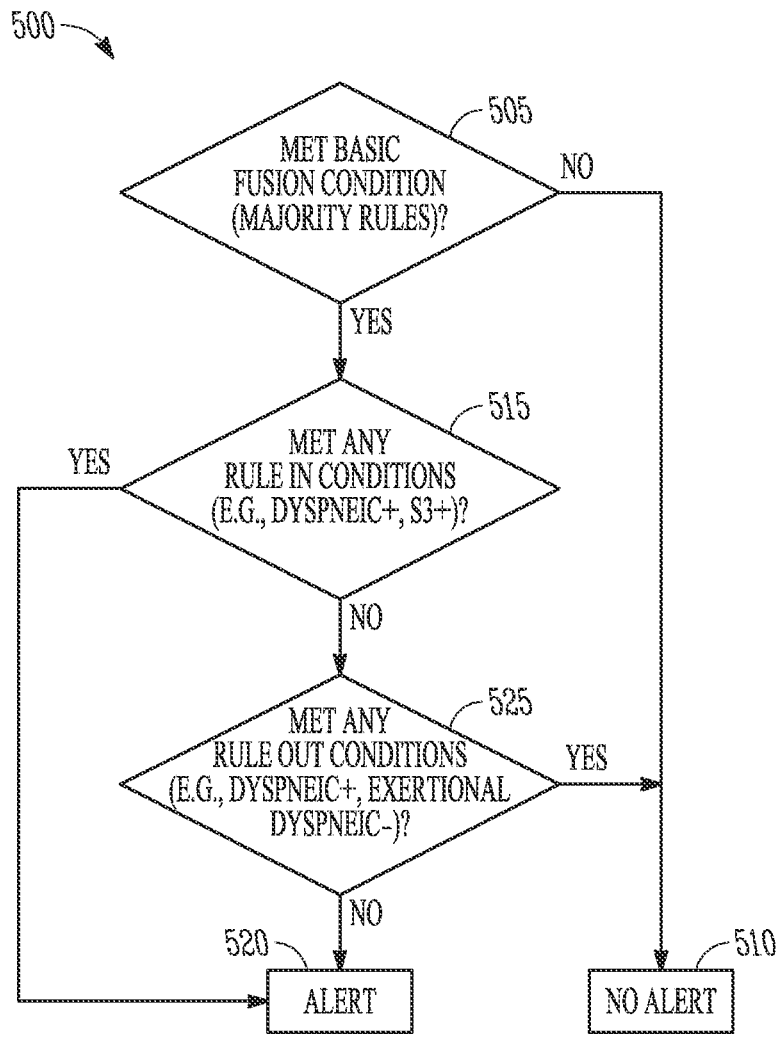
FIG. 5 is a flow diagram of an example of another method to determine whether a change occurred in the status of HF of a subject.

FIG. 5 is a flow diagram of an example of another method to determine whether a change occurred in the status of HF of a subject. Again, the method 500 applies binary or ternary decision making to the sensor outputs. At block 505, it is determined whether the sensor outputs satisfy a basic, or first, sensor fusion condition rule for HF (e.g., a majority rule). If not, flow is directed to no alert at block 510. If the basic condition is met, it is determined whether secondary conditions exist that alter the basic sensor fusion condition output. At block 515, it is determined whether conditions exist to rule in a change in HF status, such as the sensor indications showing that the subject is dyspneic and that the subject exhibits an S3 heart sound. If a Rule In condition is met, an alert is generated at 520. At block 525, it is determined whether conditions exist to rule out a change in HF and override the basic condition rule for HF, such as the subject being dyspneic, but not exertional dyspneic. If no Rule Out condition is met, an alert is generated at block 520. If a Rule Out condition is met, flow is directed to no alert at block 510.

According to some examples, logic more detailed than binary can be used to weight the output from an individual sensor. Table 2 shows another example of sensor fusion to determine a change in HF status. Again, four sensors are shown in the example, a heart sound sensor, an ITTI sensor, a respiration sensor, and a PRA sensor. Ternary logic instead of binary logic is used to determine the indication from an individual sensor. Instead of a simple positive or negative indication from the sensor, the physiological change event detection module 215 weights the outputs of the sensor as low, medium, or high according to the sensor signal by a comparison to one or more thresholds. The HF detection module then weights the strength of the indication of a change in HF using the weighted sensor outputs.

TABLE 2

| S3 | ITTI | Resp | PRA | Alert | Logic | Exceptions |
|----|------|------|-----|-------|-------|------------|
| H  | H    | H    | H   | Red   | 2 H   |            |
| H  | H    | H    | M   | Red   | 2 H   |            |
| H  | H    | H    | L   | Red   | 2 H   | S3 high spec overrides PRA high NPV |
| H  | H    | M    | H   | Red   | 2 H   |            |
| H  | H    | M    | M   | Red   | 2 H   |            |
| H  | H    | M    | L   | Red   | 2 H   | S3 high spec overrides PRA high NPV |
| H  | H    | L    | H   | Red   | 2 H   |            |
| H  | H    | L    | M   | Red   | 2 H   |            |
| H  | H    | L    | L   | Red   | 2 H   |            |

TABLE 2-continued

| S3 | ITTI | Resp | PRA | Alert | Logic | Exceptions |
|---|---|---|---|---|---|---|
| H | M | H | H | Red | 2 H | |
| H | M | H | M | Red | 2 H | S3 high spec overrides PRA high NPV |
| H | M | H | L | Red | 2 H | S3 high spec overrides PRA high NPV |
| H | M | M | H | Red | 2 H | |
| H | M | M | M | Red | 1 H + 2 M | |
| H | M | M | L | Red | 1 H + 2 M | S3 high spec overrides PRA high NPV |
| H | M | L | H | Red | 2 H | |
| H | M | L | M | Red | 1 H + 2 M | |
| H | M | L | L | Yellow | 1 H + 1 M | |
| H | L | H | H | Red | 2 H | |
| H | L | H | M | Red | 2 H | S3 high spec overrides PRA high NPV |
| H | L | H | L | Red | 2 H | S3 high spec overrides PRA high NPV |
| H | L | M | H | Red | 2 H | |
| H | L | M | M | Yellow | 1 H + 1 M | |
| H | L | M | L | Yellow | 1 H + 1 M | |
| H | L | L | H | Red | 2 H | |
| H | L | L | M | Yellow | 1 H + 1 M | |
| H | L | L | L | Yellow | 1 H | |
| M | H | H | H | Red | 2 H | |
| M | H | H | M | Yellow | 2 H | PRA high NPV overrides S3 high spec |
| M | H | H | L | Yellow | 2 H | PRA high NPV overrides S3 high spec |
| M | H | M | H | Red | 2 H | |
| M | H | M | M | Red | 1 H + 2 M | |
| M | H | M | L | Yellow | 1 H + 2 M | PRA high NPV overrides S3 high spec |
| M | H | L | H | Red | 2 H | |
| M | H | L | M | Red | 1 H + 2 M | |
| M | H | L | L | Yellow | 1 H + 1 M | |
| M | M | H | H | Red | 1 H + 2 M | |
| M | M | H | M | Yellow | 1 H + 2 M | PRA high NPV overrides S3 high spec |
| M | M | H | L | Yellow | 1 H + 2 M | PRA high NPV overrides S3 high spec |
| M | M | M | H | Red | 1 H + 2 M | |
| M | M | M | M | Red | 3 M | |
| M | M | M | L | Red | 3 M | |
| M | M | L | H | Red | 1 H + 2 M | |
| M | M | L | M | Red | 3 M | |
| M | M | L | L | Yellow | 2 M | |
| M | L | H | H | Yellow | 1 H + 1 M | |
| M | L | H | M | Yellow | 1 H + 1 M | |
| M | L | H | L | Green | 1 H + 1 M | PRA high NPV rules |
| M | L | M | H | Yellow | 1 H + 1 M | |
| M | L | M | M | Yellow | 2 M | |
| M | L | M | L | Green | 2 M | PRA high NPV rules |
| M | L | L | H | Yellow | 1 H + 1 M | |
| M | L | L | M | Yellow | 2 M | |
| M | L | L | L | Green | 1 M | |
| L | H | H | H | Red | 2 H | |
| L | H | H | M | Red | 2 H | |
| L | H | H | L | Yellow | 2 H | PRA high NPV rules |
| L | H | M | H | Red | 2 H | |
| L | H | M | M | Yellow | 1 H + 1 M | |
| L | H | M | L | Yellow | 1 H + 1 M | |
| L | H | L | H | Red | 2 H | |
| L | H | L | M | Yellow | 1 H + 1 M | |
| L | H | L | L | Yellow | 1 H | |
| L | M | H | H | Yellow | 1 H + 1 M | |
| L | M | H | M | Green | 1 H + 1 M | PRA high NPV rules |
| L | M | H | L | Green | 1 H + 1 M | PRA high NPV rules |
| L | M | M | H | Yellow | 1 H + 1 M | |
| L | M | M | M | Yellow | 2 M | |
| L | M | M | L | Green | 2 M | PRA high NPV rules |
| L | M | L | H | Yellow | 1 H + 1 M | |
| L | M | L | M | Yellow | 2 M | |
| L | M | L | L | Green | 1 M | |
| L | L | H | H | Yellow | 1 H | |
| L | L | H | M | Green | PRA high NPV | PRA high NPV rules |
| L | L | H | L | Green | PRA high NPV | PRA high NPV rules |
| L | L | M | H | Yellow | 1 H | |
| L | L | M | M | Green | Resp not specific | |
| L | L | M | L | Green | Resp not specific | PRA high NPV rules |
| L | L | L | H | Yellow | 1 H | |
| L | L | L | M | Green | PRA not specific | |
| L | L | L | L | Green | nothin to alert | |

Table 3 shows an example of indications for worsening heart failure from each sensor. The outputs of the sensors are quantified or binned into three ranges indicating low, medium, or high indications. Finer gradations can be implemented by adding additional bins or ranges. In the example, the heart sound sensor output is quantified according to the measured amplitude of the S3 heart sound. The ITTI sensor output is quantified according to a change in measured impedance. The respiration sensor output is quantified according to a change in respiration measured as breaths per minute. The PRA sensor is quantified according to the change in the patient's PRA.

TABLE 3

| Sensors | High probability | Medium probability | Low probability |
|---|---|---|---|
| S3 | Amplitude change > 150%, or Amplitude > 15 mg | Amplitude change in the range of 100-150% | Amplitude change < 100% |
| ITTI | Impedance change > 15% | Impedance change in the range 10-15% | Impedance change < 10% |
| Resp | Rate change ≥ 8 bpm | Rate change in the range of 4-8 bpm | Rate change < 4 bpm |
| PRA | PRA change > 30% | PRA change in the range of 15-30% | PRA change < 15% |

In some examples, the outputs are weighted according to the likelihood that the sensor signal indicates worsening HF. When the outputs of the sensor are weighted, the HF detection module 220 applies the first rule to the weighted physiological change events to blend the sensor outputs and determine a likelihood that the change in HF status.

In the example of Table 2, under the first rule there is a strong or high likelihood of worsening HF when i) two or more sensors indicate a high likelihood of HF, or ii) one sensor indicates high likelihood and two sensors indicate medium likelihood, or iii) three or more sensors indicate medium likelihood. Table 2 shows that a Red Alert is indicated when one of these conditions occurs. Thus the alert includes an indication of the likelihood that the change in HF status occurred, with "Red" being the strongest indication. There is a medium indication of worsening HF when i) one sensor indicates a high likelihood of HF and one sensor indicates a medium likelihood, ii) one sensor indicates high likelihood, or iii) two sensors indicate medium likelihood. Table 2 shows that a Yellow Alert is indicated when one of these conditions occurs to indicate a medium likelihood of worsening HF. There is a low indication of worsening when i) only one sensor indicates a medium likelihood and the other sensor indicate low likelihood, or iii) all the sensors indicate low likelihood. This logic of the first rule is exemplary and the logic can be adjusted according to physician preference or according to a patient's unique requirements.

The second rule may then override the determinations of the first rule. For example, a low indication from the PRA sensor may override a medium indication of one or both of the ITTI sensor and the Respiration sensor as shown in line 69 of Table 2, or may override a high indication of the ITTI sensor or the Respiration sensor, as shown in line 48 of Table 2. In another example, a medium or high indication of an S3 heart sound indicated by the heart sound sensor overrides a low indication of the PRA sensor as shown in line 15 of Table 2.

In some examples, the HF detection module 220 declares whether there is a high, medium, or low indication of worsening HF and provides the alert based on the declared HF event. Thus, the HF detection module determines a level of urgency of the alert according to the first and second rules.

The above described multi-sensor fusion logic enhances the positive prediction of worsening HF by the array of diagnostic sensors included in the device 200. Other sensors, either implantable or external, can be used in the device 200 in FIG. 2 to monitor for HF instead of, or in addition to, those discussed previously. In some examples, the device 200 includes an implantable cardiac pressure sensor to measure chamber pressure of the left ventricle. A decrease in chamber pressure may be indicative of worsening HF.

In an example, a pressure sensor is implanted in a coronary vessel to determine left ventricle pressure by direct measurement of coronary vessel pressure. A description of systems and methods that use such an implantable pressure sensor is found in Salo et al., U.S. Pat. No. 6,666,826, entitled "Method and Apparatus for Measuring Left Ventricular Pressure," filed Jan. 4, 2002, which is incorporated herein by reference in its entirety. Other cardiac pressure sensors examples include a right ventricle (RV) chamber pressure sensor, a pulmonary artery pressure sensor, and a left atrial chamber pressure sensor. A change in heart chamber pressure may also be evident in heart sounds, and therefore a heart sound sensor may be used to deduce a change in pressure.

In some examples, the sensors 210 include an implantable heart rate sensor. In certain example, the heart rate sensor includes the previously mentioned circuits and electrodes to sense an electrogram signal representative of heart depolarizations. A heart sound sensor may be used to sense heart rate as well, such as by measuring intervals between S2 heart sounds for example.

In some examples, the sensors 210 include an implantable oxygen saturation sensor. An oxygen saturation sensor produces an electrical sensor signal proportional to the oxygen saturation of blood, which could be reduced with worsening HF due to inadequate gas exchange in the presence of one or both of pulmonary congestion and decreased oxygen delivery to tissues. An approach for using an implantable sensor to measure blood oxygen saturation levels is found in Thompson, U.S. Pat. No. 5,342,406, entitled "Oxygen Sensor Based Capture Detection for a Pacer," filed Oct. 7, 1992, which is incorporated herein by reference in its entirety.

In some examples, the sensors 210 include an implantable cardiac temperature sensor. In some examples, the implantable cardiac temperature sensor is included in a lead system implanted into the coronary sinus of a patient. The implantable cardiac temperature sensor measures the temperature of the blood returning through the coronary sinus after having passed through myocardial tissue. As a byproduct of normal cardiac function, the heart generates heat. This heat is extracted by the perfusing blood. The blood exits through the coronary veins into the coronary sinus before passing into the right atrium and right ventricle. The blood is then pumped through the lungs where the excess heat is removed and passed out of the body with the exhaled air.

The useful work ($W_u$) performed by the left ventricle relates to the volume of blood moved through the ventricle, whereas the heat output from the left ventricle is related to total work ($W_T$). The difference in temperature between blood entering the left ventricle and blood in a coronary vein is related to left ventricular work. An increase in $W_T$, or cardiac temperature as a surrogate measurement, that is not accompanied by other indications of increased activity or patient exertion may indicate a lowering of efficiency of a patient's hemodynamic system due to worsening HF.

An approach to sensing temperature within a coronary vein is found in Salo, Patent Application Publ. No. 2003/0125774, entitled "Method and Apparatus for Monitoring Left Ventricular Work or Power," filed Dec. 31, 2001, which is incorporated herein by reference in its entirety.

In some examples, the sensors 210 include a blood flow sensor. Examples of a blood flow sensor include a cardiac output sensor circuit or a stroke volume sensor circuit. Examples of stroke volume sensing are discussed in Salo et al., U.S. Pat. No. 4,686,987, "Biomedical Method And Apparatus For Controlling The Administration Of Therapy To A Patient In Response To Changes in Physiologic Demand," filed Mar. 29, 1982, and in Hauck et al., U.S. Pat. No. 5,284,136, "Dual Indifferent Electrode Pacemaker," filed May 13, 1991, which are incorporated herein by reference in their entirety.

Figure 6:
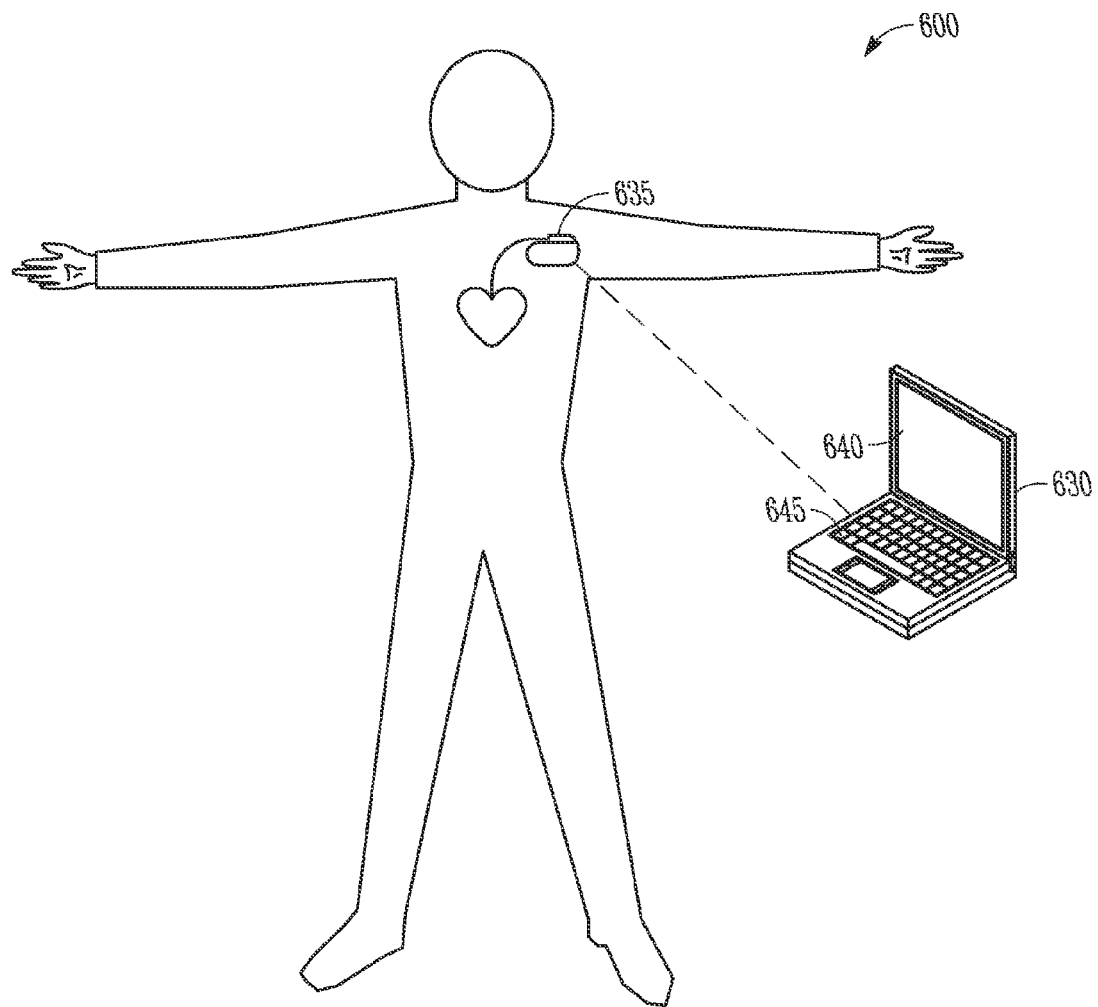
FIG. 6 is an illustration of a system that includes an external device used to program parameters of an IMD.

In some examples, the sensors 210 and the processor 205 are included in an IMD based system. FIG. 6 is an illustration of a system 600 that includes an external device 630 used to program parameters of an IMD 635. The external device 630 includes a programming interface such as a display 640 and/or a keyboard 645 or computer mouse. The external device 630 communicates with the IMD 635 wirelessly. The IMD 635 communicates the alert to the external device 630 to present the alert to a user. In some examples, the external device 630 communicates the level of urgency of the alert to the user, such as by displaying a high, medium or low alert as a Red, Yellow, or Green Alert respectively. In some examples, at least one sensor is external and communicates information to the IMD 635 wirelessly.

Figure 7:
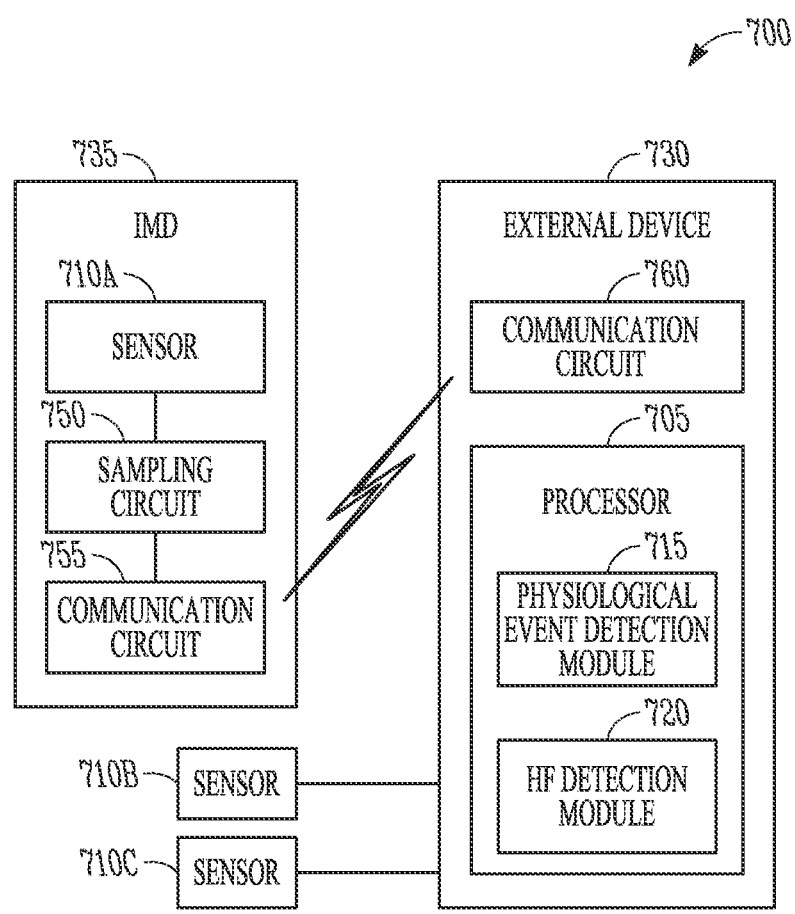
FIG. 7 is an example of a system to monitor for HF of a subject.

FIG. 7 is an example of a system 700 to monitor for HF of a subject. The system 700 includes a plurality of sensors 710A, 710B, 710C. Each of the sensors 710A, 710B, 710C provides a sensor signal that includes physiological information.

The sensors may include combinations of any of the sensors described herein. The system 700 also includes an IMD 735 that includes at least one of the sensors 710A. The IMD 735 includes a sampling circuit 750 to sample a sensor signal, such as to generate digital values to represent the sensor output. The IMD 735 also includes first communication circuit 755 to communicate the sampled sensor signal to a second device.

The system further includes an external device 730. The external device includes a second communication circuit 760 to communicate with the IMD 735 wirelessly, and a processor 705. The processor 705 includes a physiological change event detection module 715 and an HF detection module 720. The IMD 735 communicates a sampled sensor signal to the external device 730. In some example, the sampled sensor signal is communicated to the external device 730 via a third device such as a repeater. The repeater is local to the IMD 735, such as by being in the same room as the patient, allowing the external device 730 to be remote from the patient. The physiological change event detection module 715 detects an event from a sensor signal provided by one or all of the sensors 710A, 710B, 710C, and determines whether a detected event is indicative of a change in HF status. The HF detection module declares whether the change in HF status occurred according to the first and second rules.

A medical device system that includes a suite of sensors and multi-sensor fusion logic to blend the sensor indications enhances the positive prediction and detection of worsening HF.

The above detailed description includes references to the accompanying drawings, which form a part of the detailed description. The drawings show, by way of illustration, specific embodiments in which the invention can be practiced. These embodiments are also referred to herein as "examples." All publications, patents, and patent documents referred to in this document are incorporated by reference herein in their entirety, as though individually incorporated by reference. In the event of inconsistent usages between this document and those documents so incorporated by reference, the usage in the incorporated reference(s) should be considered supplementary to that of this document; for irreconcilable inconsistencies, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In the appended claims, the terms "including" and "in which" are used as the plain-English equivalents of the respective terms "comprising" and "wherein." Also, in the following claims, the terms "including" and "comprising" are open-ended, that is, a system, device, article, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

Method examples described herein can be machine or computer-implemented at least in part. Some examples can include a computer-readable medium or machine-readable medium encoded with instructions operable to configure an electronic device to perform methods as described in the above examples. An implementation of such methods can include code, such as microcode, assembly language code, a higher-level language code, or the like. Such code can include computer readable instructions for performing various methods. The code can form portions of computer program products. Further, the code can be tangibly stored on one or more volatile or non-volatile computer-readable media during execution or at other times. These computer-readable media can include, but are not limited to, hard disks, removable magnetic disks, removable optical disks (e.g., compact disks and digital video disks), magnetic cassettes, memory cards or sticks, random access memories (RAM's), read only memories (ROM's), and the like.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. §1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description, with each claim standing on its own as a separate embodiment. The scope of the invention should be determined with reference to the appended claims, along with the full scope of equivalents to which such claims are entitled.

What is claimed is:

1. A system comprising:
a plurality of sensors, each sensor configured to provide a sensor signal, wherein the sensor signal includes physiological information;
an implantable device comprising:
   at least one of the sensors;
   a sampling circuit, communicatively coupled to the implantable sensors, configured to provide a sampled sensor signal; and
   a first communication circuit, communicatively coupled to the sampling circuit, configured to communicate the sampled sensor signal to a second device; and
an external device comprising:
   a second communication circuit configured to communicate with the implantable device; and
   a processor, communicatively coupled to the second communication circuit, wherein the processor includes:
      a physiological change event detection module configured to:
         detect a physiological change event from a sensor signal including at least one sampled sensor signal communicated from the implantable device; and
         produce an indication of occurrence of one or more physiological change events; and
      a heart failure (HF) detection module configured to:
         determine whether the detected physiological change events are indicative of a change in HF status using a first rule;
         determine whether to override the first rule HF determination using a second rule; and
         generate an indication of whether the change in HF status occurred according to the first and second rules.

2. The system of claim 1, wherein the first rule includes indicating a change in HF status when a majority of a set of detectable physiological change events is detected.

3. The system of claim 2, wherein the second rule includes:
overriding a negative first rule HF determination according to a specificity of a detected physiological change event; and
overriding a positive first rule HF determination according to a negative predictive value of a physiological change event.

4. The system of claim 1, wherein the first rule includes indicating the change in HF status when a majority of a set of detectable physiological change events is detected.

5. The system of claim 1, wherein the second rule includes overriding a negative first rule HF determination when a condition for an S3 heart sound is met in a heart sound signal.

6. The system of claim 1, wherein the second rule includes overriding a positive first rule HF determination when a condition in a physiologic response to patient activity is met.

7. The system of claim 1, wherein the HF detection module weights the second rule HF determination greater than the first rule HF determination.

8. The system of claim 1,
wherein the physiological change event detection module is configured to weight the detected physiological change event according to the sensor signal, and
wherein the HF detection module is configured to:
   determine a likelihood that the change in HF status occurred using the weight of the physiological change event; and
   provide an alert based on the declared HF event, wherein the alert includes an indication of the likelihood that the change in HF status occurred.

9. The system of claim 8, wherein the HF detection module is configured to determine a level of urgency of the alert according to the first and second rules.

10. The system of claim 8, wherein the HF detection module is configured to generate an indication of one of a plurality of levels of urgency of the alert according to the first and second rules.

11. The system of claim 1, wherein the plurality of sensors includes at least one of:
an implantable impedance sensor, an implantable respiration sensor, and an implantable intra-thoracic total impedance (ITTI) sensor.

12. The system of claim 1, wherein the plurality of sensors includes at least one of an implantable activity sensor and an implantable electrocardiogram sensor.

13. The system of claim 1, wherein the plurality of sensors includes an implantable heart sound sensor.

14. The system of claim 1, wherein the plurality of sensors includes at least one of:
an implantable blood pressure sensor;
an implantable oxygen saturation sensor;
an implantable blood flow sensor; and
an implantable temperature sensor.

15. The system of claim 1, wherein the physiologic change detector is configured to detect a physiological change event related to total work of the lett ventricle using a sensor signal including at least one sampled sensor signal communicated from the implantable device.

16. The system of claim 1,
wherein the physiological change event detection module is configured to:
   compare a sensor signal from a sensor of the plurality of sensors to a specified threshold; and
   assign one indication of a plurality of indications of occurrence of a physiological change event to the sensor signal according to the comparison;
wherein the HF detection module is configured to:
   accumulate indications assigned to the sensors signals provided by plurality of sensors; and
   determine whether the detected physiological change events are indicative of a change in HF status using the accumulated indications.

17. The system of claim 16, wherein the detection module is configured to assign a weight to the indication of a change in HF status using the accumulated indications assigned to the sensor signals.

18. The system of claim 16, wherein the physiological change event detection module is configured to assign one of three or more indications of a physiological change event to the sensor signal according to a comparison to a plurality of specified thresholds.

19. The system of claim 16, wherein the HF detection module is configured to override indications assigned to a first set of sensor signals according to an indication assigned to a sensor signal different from the first set of sensor signals.

20. The system of claim 16, wherein an indication assigned to a sensor signal is reflective of a strength of the indication of the occurrence of a physiological change event, and wherein the HF detection module is configured to assign the weight to the indication of a change in HF status using the accumulated strength indications assigned to the sensor signals.

* * * * *